United States Patent [19]

Oxenrider et al.

[11] Patent Number: 4,537,728

[45] Date of Patent: Aug. 27, 1985

[54] FLUORINATED AND NON-FLUORINATED TERMINALLY HALOGENATED ALKYL PYROMELLITATES

[75] Inventors: Bryce C. Oxenrider, Florham Park; David J. Long, Stanhope, both of N.J.

[73] Assignee: Allied Corporation, Morris Township, Morris County, N.J.

[21] Appl. No.: 431,452

[22] Filed: Sep. 30, 1982

[51] Int. Cl.$^3$ .................... C07C 153/07; C07C 69/76; C07C 101/20; C07C 101/24; C07C 101/26

[52] U.S. Cl. .................... 260/455 R; 8/115.6; 252/8.6; 252/8.7; 252/8.75; 252/8.8; 427/393.4; 524/219; 524/239; 524/240; 524/282; 524/283; 524/287; 524/294; 560/37; 560/38; 560/41; 560/87

[58] Field of Search .................... 560/37, 41, 87, 38; 564/153; 260/455 R; 252/8.6, 8.75, 8.8, 8.7; 8/115.6; 427/393.4; 524/219, 239, 240, 282, 283, 287, 294

[56] References Cited

U.S. PATENT DOCUMENTS

| 3,870,748 | 3/1975 | Katsushima et al. | 560/87 |
| 4,190,545 | 2/1980 | Marshall et al. | 252/8.75 |
| 4,192,754 | 3/1980 | Marshall et al. | 252/8.8 |
| 4,209,610 | 6/1980 | Mares et al. | 260/40 |
| 4,329,489 | 5/1982 | Saunders et al. | 560/79 |

*Primary Examiner*—Natalie Trousof
*Assistant Examiner*—Vera C. Clarke
*Attorney, Agent, or Firm*—R. C. Stewart, II; A. M. Doernberg; G. H. Fuchs

[57] ABSTRACT

Novel polycarboxy benzene dianhydrides useful as surfactants are disclosed. The novel compounds of this invention are pyromellitate tetraesters wherein two ester moieties characteristically contain fluorinated alkyl groups or saturated hydrocarbon alkyl groups and wherein two ester moieties contain alkylene moieties having a terminal halogen.

15 Claims, No Drawings

FLUORINATED AND NON-FLUORINATED TERMINALLY HALOGENATED ALKYL PYROMELLITATES

BACKGROUND OF THE INVENTION

This invention relates to novel compounds synthesized from polycarboxy benzene dianhydrides. More specifically, the present invention relates to compounds synthesized by reacting fluorinated or hydrocarbon pyromellitate diester-diacid chlorides with alkanols having a terminal halogen. The compounds of the present invention are useful as soil and water repelling agents.

Fluorinated pyromellitates and the use of such compounds as surface modifiers is disclosed in U.S. Pat. No. 4,209,610 (Mares et al., 1980). Mares et al. discloses various pyromellitate tetraesters wherein two ester moieties contain partially fluorinated alkyl groups and wherein two ester moieties contain alkyl groups substituted with a hydroxyl group or alkyl groups substituted with a halogen and a hydroxyl group. Mares et al. also discloses a method for applying the compounds in organic solution to various fibers. A method for applying the compounds in an aqueous emulsion is disclosed in U.S. Pat. No. 4,092,754 (Marshall et al., 1980).

We have discovered that esterifying pyromellitic dianhydride with partially fluorinated alcohols and alkanols having a terminal halogen or with hydrocarbon alcohols and alkanols having a terminal halogen results in compounds which are useful as soil and water repellents. The pyromellitates of the present invention are also expected to have improved retention characteristics when applied to various fibers as opposed to the retention characteristics of previously known compounds.

BRIEF DESCRIPTION OF THE INVENTION

This invention relates to novel compounds having the structure:

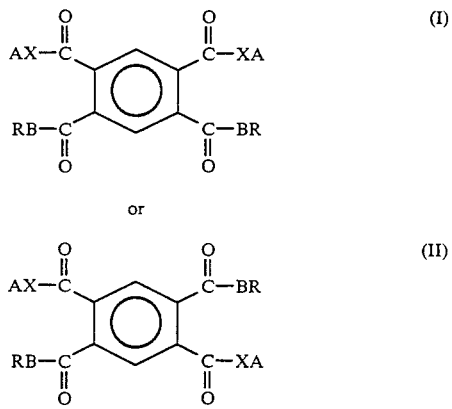

or mixtures thereof wherein X is —O—, —S—, —NH—, or —N(CH$_3$)—; wherein A is alkyl of 2-24 carbons or —R'—(CH$_2$)$_p$CF$_3$ with R' being alkylene of 1-6 carbons and p being an integer of 3-15; wherein B is —O—, —S—, —NH—, or —N(CH$_3$)— and where R is (CH$_2$)$_n$Q or (CH$_2$)$_m$CH[(CH$_2$)$_z$Q]$_2$ with n being an integer of 2-10, m being an integer of 0-10, and z being an integer of 1-5; wherein Q is Cl or Br.

The present invention also includes methods comprising applying the above composition to fibers such as polyester or polyamide fibers. Additionally, the invention includes polyester, polyamide, or other similar fibers having applied thereto the novel compounds described above.

DETAILED DESCRIPTION OF THE INVENTION

The novel compounds of the present invention are pyromellitates represented by the following general formulas:

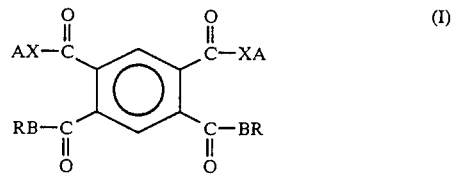

or

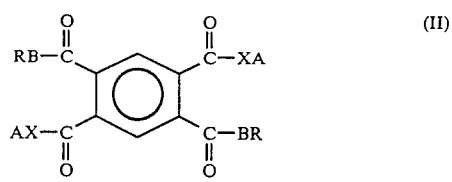

or mixtures thereof wherein X is —O—, —S—, —NH— or —N(CH$_3$)— with A being alkyl of 2 to 24 carbons or —R'—(CF$_2$)$_p$CF$_3$ where R' is alkylene of 1-6 carbons and p is an integer of 3-15; wherein B is —O—, —S—, —NH—, or —N(CH$_3$)— and where R is (CH$_2$)$_n$Q or (CH$_2$)$_m$CH[(CH$_2$)$_z$Q]$_2$ with n being an integer of 2-10, m being an integer of 0-10, and z being an integer of 1-5; wherein Q is Cl or Br.

In many preferred embodiments of this invention, pyromellitates having terminally halogenated linear or branched alkyl groups of 3-6 carbons are preferred. Substituents X and B in the above formulae are preferably oxygen, and Q may be either Cl or Br with each being equally preferred.

The pyromellitates may be synthesized by initially reacting pyromellitic anhydride with fluoroalcohols in accordance with the procedures described in U.S. Pat. No. 4,209,610 in order to obtain a diester-diacid intermediate. Fluoroamines or fluorothiols may be used instead of fluoroalcohols in order to produce diamide-diacid or dithio-diacid intermediates. Alternately, hydrocarbon alcohols, amines, or thiols may be utilized in order to obtain non-fluorinated intermediate compounds. The intermediates thus obtained may then be converted to acid chloride compounds by reacting the intermediates with a chlorinating agent such as oxalyl chloride, phosphorous pentachloride, phosgene-DMF, thionyl chloride or any other suitable chlorinating agent. This acid-chloride producing reaction should preferably be carried out at a temperature between about room temperature and about 60° C. under essentially anhydrous conditions. The synthesis of these acid chlorides is discussed more fully in the copending commonly assigned application of Oxenrider and Long Serial No. 429,947 now U.S. Pat. No. 4,460,785, filed herewith. The final step of the synthesis involves reacting the diester-diacid chloride intermediate with an alkanol having a terminal halogen in the presence of a base to obtain a pyromellitate tetraester wherein two ester moieties have a terminally halogenated alkylene group of 2–10 carbons.

The pyromellitates of the present invention are useful for applications in the general field of soil and water repellents. In particular, it is expected that the pyromellitates of the present invention will have superior retention characteristics when applied to various fibers as opposed to the retention properties of previously known soil and water repellents.

Application of pyromellitates with terminally halogenated alkyl groups to fibers is accomplished in general by contacting such fibers with a liquid emulsion, dispersion or solution which contains said pyromellitates, and thereafter usually heating said fibers sufficiently to develop soil and oil repellency. After use and cleaning, (as approximated by standard laundering tests) the retention of oil and soil repellency is expected to be superior as compared with other known soil and oil repellents, with the superior retention properties due in part to the terminally halogenated alkylene moieties.

The preferred fluorinated pyromellitates with terminally halogenated alkyl groups are those derived from fluorinated hydrocarbyl ethanols represented by the formula $CF_3(CF_2)_pCH_2CH_2O-$ where p is a commercial mixture of 3–15 or even larger, but is preferably 3–13. Slightly less preferred are those derived from fluorinated hydrocarbyl propanols and butanols. Substituents A with alkylenes of 1–6 carbons other than 1,2-ethylene, 1,2-propylene or 1-4-butylene may also be used, but are less preferred.

Pyromellitate tetraesters wherein two ester moieties have alkyl groups of 2–24 carbons and two ester moieties have alkylene groups of 2–10 carbons having a pendant (terminal) halogen are also a subject of this invention. These pyromellitates are valuable for several applications and may be referred to as hydrocarbon pyromellitates. Hydrocarbon pyromellitates having terminally halogenated alkyl moieties wherein A is alkyl of 14–24 carbons may be used alone as water repelling agents. Additionally, these pyromellitates wherein A is alkyl of 2–24 carbons may be used in admixture with fluorocarbon pyromellitates having terminally halogenated alkyl moieties in order to produce a less expensive soil repellent.

Mixtures which consist essentially of hydrocarbon pyromellitates with pendant halogens and fluorocarbon pyromellitates with pendant halogens may be formed by simply dissolving the respective hydrocarbon and fluorocarbon pyromellitates in a common solvent to form a homogeneous solution. Suitable solvents for forming the solutions include chloroform, dioxane, acetone, and other similar solvents. These mixtures will have soil and water repelling characteristics similar to solutions which contain only fluorinated compounds. However, these mixtures are less expensive to produce, since the hydrocarbon diluent is not as expensive as the fluorocarbon component.

Fibers having the compositions of the present invention applied thereto are also a subject of the present invention. Suitable fibers are polycaproamide, poly(hexamethylene diamine adipate) and poly(ethylene terephthalate) or other similar polyamides or polyesters.

EXAMPLES

Three mixtures (A, B, and C) of the meta and para isomers of the diester-diacid of pyromellitic dianhydride were prepared and isolated in accordance with the procedures of U.S. Pat. No. 4,252,982 to Oxenrider. This diester-diacid is represented by the formulae:

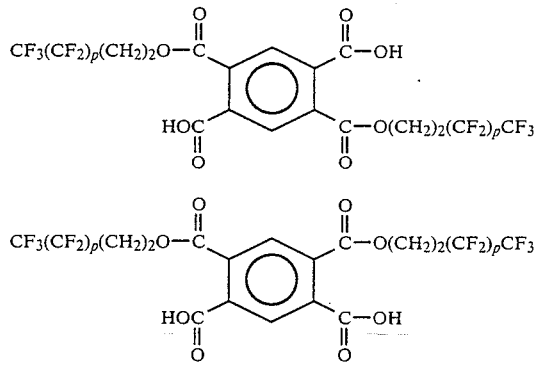

The values for p were 5, 7, 9 and 11 since a mixture of fluorinated alcohols had been used. Each mixture was then titrated according to standard procedures in order to determine the gram equivalent weight of acid for each mixture. The results are in Table I.

TABLE I

| Mixture | (COOH) meq/g |
|---------|--------------|
| A | 1.65 |
| B | 1.71 |
| C | 1.64 |

EXAMPLE 1

A portion of mixture A (20 g, 33 meq) was suspended in ethyl acetate (100 mL) under nitrogen at 40° C. in a round bottom flask. A solution of oxalyl chloride (3.0 mL, 33 mmol) in dry ethyl acetate (20 mL) was prepared and added to the suspended diester-diacid. The resultant reaction mixture was stirred for 3 hours at 50° C. At this stage of the reaction, the diester-diacid has been converted to a diester-diacid chloride which is in solution. A mixture of 3-chloro-1-hydroxypropane (2.8 mL, 33 mmol) and triethylamine (5.0 mL) in ethyl acetate (20 mL) was added to the diester-diacid chloride solution over a period of 5 minutes. This reaction mixture was stirred at 50° C. for 2 hours and then stirred at room temperature for 18 hours. The reaction mixture was filtered and evaporated on a rotary evaporator to yield a semisolid brown product (21.0 g). The structure was confirmed by proton NMR. The product had a surface tension of 14 dynes/cm as determined by the Zisman technique.

EXAMPLE 2

A portion of mixture B (25.0 g, 43 meq) was suspended in ethyl acetate (90 mL) under nitrogen at 50° C. in a round bottom flask. A solution of oxalyl chloride (7.4 mL, 86 mmol) in ethyl acetate (10 mL) was prepared and rapidly added to the suspended diester-diacid. The resultant reaction mixture was stirred at 50° C. for 2 hours. The reaction mixture was flash evaporated and a dark brown residue was obtained. At this stage of the reaction, the diester-diacid has now been converted to a diester-diacid chloride. The diester-diacid chloride was dissolved in ethyl acetate (100 mL) and stirred at 50° C. A separate mixture of 3-bromo-1-propanol (4.1 mL, 43 mmol) and triethylamine (6.3 mL) in ethyl acetate (20 mL) was prepared and added to the diester-diacid chloride over a period of 5 minutes. This reaction mixture was stirred at 50° C. for 2 hours and then stirred at room temperature for a period of 18 hours. The product mixture was filtered and evaporated on a rotary evaporator to yield a dark brown product (28 g). The structure of the product was confirmed by proton NMR. The product had a surface energy of 12 dynes/cm.

EXAMPLE 3

A portion of mixture C (25.0 g, 41 meq) was suspended in ethyl acetate (90 mL) under nitrogen at 50° C. in a round bottom flask. A solution of oxalyl chloride (7.1 mL, 82 mmol) in ethyl acetate was prepared and added to the suspended diester-diacid over a period of 3 minutes. The resultant reaction mixture was stirred at 50° C. for 2 hours. The reaction was not complete as some insoluble foam remained. A solution of oxalyl chloride (3.5 mL, 41 mmol) in ethyl acetate (5 mL) was prepared and added to the reaction mixture over a 1 minute period. The reaction mixture was stirred for 1 hour at 40° C. The mixture containing the product diester-diacid chloride was filtered and evaporated on a rotary evaporator to obtain a dark brown residue. The residue (diester-diacid chloride) was dissolved in ethyl acetate (100 mL) and stirred at 50° C. A separate reactant mixture of 6-chloro-1-hexanol (4.9 mL, 41 mmol) in triethylamine (6.3 mL) in ethyl acetate (20 mL) was prepared and added to the diester-diacid chloride solution over a period of 5 minutes. The reaction mixture was stirred at 50° C. for 2 hours and then stirred at room temperature for 16 hours. The product mixture was filtered and evaporated on a rotary evaporator to yield a brown viscous (29.0 g) product. The structure of the pyromellitate was confirmed by proton NMR. The surface energy was determined to be 13 dynes/cm by the Zisman technique.

EXAMPLE 4

A portion of mixture C (25.0 g, 41 meq) was suspended in ethyl acetate (90 mL) under nitrogen at 50° C. in a round bottom flask. A solution of oxalyl chloride (7.1 mL, 82 mmol) in ethyl acetate was prepared and added to the suspended diester-diacid over a period of 3 minutes. The resultant reaction mixture was stirred at 50° C. for 2 hours. The reaction was not complete as some insoluble foam remained. A solution of oxalyl chloride (3.5 mL, 41 mmol) in ethyl acetate (5 mL) was prepared and added to the reaction mixture over a 1 minute period. The reaction mixture was stirred for 1 hour at 40° C. The mixture containing the product diester-diacid chloride was filtered and evaporated on a rotary evaporator to obtain a dark brown residue. The residue (diester-diacid chloride) was dissolved in ethyl acetate (100 mL) and stirred at 50° C. A separate reactant mixture of 1,3-dichloro-2-propanol (4.1 mL, 41 mmol) in triethylamine (6.3 mL) in ethyl acetate (20 mL) was prepared and added to the diester-diacid chloride solution over a period of 5 minutes. The reaction mixture was stirred at 50° C. for 2 hours and then stirred at room temperature for 16 hours. The product mixture was filtered and evaporated on a rotary evaporator to yield a brown viscous (29.0 g) product. The structure of the pyromellitate was confirmed by proton NMR. The surface energy was determined to be 11 dynes/cm by the Zisman technique.

We claim:

1. A monocyclic compound having the structure:

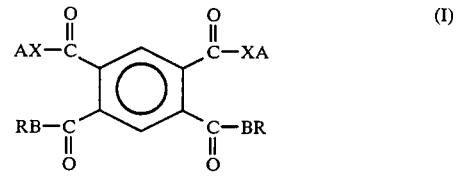

(I)

or

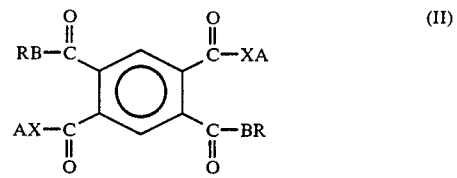

(II)

or mixtures thereof wherein X is independently at each occurrence —O—, —S—, —N(CH$_3$)— or —NH—; wherein A is alkyl of 2-24 carbons or R'—(CF$_2$)$_p$CF$_3$ with R' being alkylene of 1-6 carbons and p being an integer of 3-15; wherein B is —O—, —S—, —NH—, or —N(CH$_3$)—; wherein R is (CH$_2$)$_n$Q or (CH$_2$)$_m$CH$_2$ with n being an integer of 2-10, m being an integer of 0-10, and z being an integer of 1-5; wherein Q is Cl or Br.

2. Compound of claim 1 wherein R is (CH$_2$)$_n$Q.
3. Compound of claim 2 wherein Q is Cl.
4. Compound of claim 2 wherein Q is Br.
5. Compound of claim 3 or 4 wherein n is an integer of 3-6.
6. Compound of claim 5 wherein n is 3.
7. Compound of claim 5 wherein n is 6.
8. Compound of claim 1 wherein R is (CH$_2$)$_m$CH$_2$.
9. Compound of claim 8 wherein m=0 and z=1.
10. Compound of claim 9 wherein Q is chloro.
11. Compound of claim 1 wherein B is —O—.
12. Compound of claim 1 wherein X is —O—.
13. Compound of claim 1 wherein A is —R'—(CH$_2$)$_p$CF$_3$.
14. Compound of claim 13 wherein R' is —CH$_2$CH$_2$—.
15. Compound of claim 14 wherein p is 3-13.

* * * * *

UNITED STATES PATENT AND TRADEMARK OFFICE
CERTIFICATE OF CORRECTION

PATENT NO. : 4,537,728
DATED : August 27, 1985
INVENTOR(S) : Bryce C. Oxenrider and David J. Long It is certified that error appears in the above-identified patent and that said Letters Patent are hereby corrected as shown below:

Col. 6, line 47, "$(CH_2)_m CH_2$" should read

-- $(CH_2)_m CH [(CH_2)_z Q]_2$ --

Col. 6, line 50, "-0-" (zero) should read -- -O- -- (letter "O")

Col. 6, lines 52 and 53, "$R'-(CH_2)_p CF_3$" should read

-- $R'(CF_2)_p CF_3$ --

Signed and Sealed this

Twenty-fourth Day of December 1985

[SEAL]

Attest:

DONALD J. QUIGG

Attesting Officer    Commissioner of Patents and Trademarks